(12) United States Patent
Everman et al.

(10) Patent No.: US 12,033,042 B2
(45) Date of Patent: Jul. 9, 2024

(54) APPARATUS FOR BIAS ELIMINATED PERFORMANCE DETERMINATION

(71) Applicant: GMECI, LLC, Beavercreek, OH (US)

(72) Inventors: Brad R. Everman, Haddonfield, NJ (US); Brian Scott Bradke, Brookfield, VT (US)

(*) Notice: Subject to any disclaimer, the term of this patent is extended or adjusted under 35 U.S.C. 154(b) by 0 days.

(21) Appl. No.: 17/959,439

(22) Filed: Oct. 4, 2022

(65) Prior Publication Data

US 2024/0112078 A1   Apr. 4, 2024

(51) Int. Cl.
    G06N 20/00    (2019.01)
(52) U.S. Cl.
    CPC ................. G06N 20/00 (2019.01)
(58) Field of Classification Search
    None
    See application file for complete search history.

(56) References Cited

U.S. PATENT DOCUMENTS

| | | |
|---|---|---|
| 11,304,657 B2 | 4/2022 | Bower |
| 11,592,791 B1* | 2/2023 | Wiegman ............. G05B 13/041 |
| 2019/0042894 A1 | 2/2019 | Anderson |
| 2022/0061757 A1 | 3/2022 | De |
| 2023/0035334 A1* | 2/2023 | Everman ................ A61B 5/486 |
| 2023/0057311 A1* | 2/2023 | Moeykens ........... G08G 5/0013 |

FOREIGN PATENT DOCUMENTS

WO   WO-2019175425 A1 *  9/2019   ......... A63B 24/0006

* cited by examiner

*Primary Examiner* — David R Vincent
(74) *Attorney, Agent, or Firm* — Caldwell Intellectual Property Law

(57) ABSTRACT

In an aspect, an apparatus for bias eliminated performance determination is presented. An Apparatus includes at least a processor and a memory communicatively connected to the at least a processor. A memory includes instructions configuring at least a processor to receive, through a sensing device, biological feedback of a user. At least a processor is configured to compare biological feedback to a performance parameter of a task. At least a processor is configured to generate, as a function of a comparison, a performance determination through a performance determination machine learning model. At least a processor is configured to classify a performance determination to a bias category as a function of a bias classifier. At least a processor is configured to train a performance determination machine learning model with biological feedback and a bias classification of a performance determination.

16 Claims, 7 Drawing Sheets

– 1 –

APPARATUS FOR BIAS ELIMINATED PERFORMANCE DETERMINATION

FIELD OF THE INVENTION

The present invention generally relates to the field of performance determination. In particular, the present invention is directed to an apparatus for bias eliminated performance determination.

BACKGROUND

Machine learning models are prone to incorporating human biases when generating outputs. Performance determination using machine learning models can therefore be improved.

SUMMARY OF THE DISCLOSURE

In an aspect, an apparatus for bias eliminated performance determination is presented. An Apparatus includes at least a processor and a memory communicatively connected to the at least a processor. A memory includes instructions configuring at least a processor to receive, through a sensing device, biological feedback of a user. At least a processor is configured to compare biological feedback to a performance parameter of a task. At least a processor is configured to generate, as a function of a comparison, a performance determination through a performance determination machine learning model. At least a processor is configured to classify a performance determination to a bias category as a function of a bias classifier. At least a processor is configured to train a performance determination machine learning model with biological feedback and a bias classification of a performance determination.

In another aspect, a method of bias eliminated performance determination using a computing device is presented. A method includes receiving, through a sensing device, biological feedback of a user. A method includes comparing, at a computing device, biological feedback to a performance parameter of a task. A method includes generating, as a function of a comparison, a performance determination through a performance determination machine learning model. A method includes classifying a performance determination to a bias category as a function of a bias classifier. A method includes training a performance determination machine learning model with biological feedback and a bias classification of a performance determination.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for bias elimination in performance determinations. In an embodiment, an apparatus for eliminating bias in performance determination machine learning models is presented.

Aspects of the present disclosure can be used to provide accurate performance determinations of biologically diverse people. Aspects of the present disclosure can also be used to improve accuracy of performance determination machine learning models.

Aspects of the present disclosure allow for eliminating bias from performance determinations. Exemplary embodiments illustrating aspects of the present disclosure are described below in the context of several specific examples.

Figure 1:
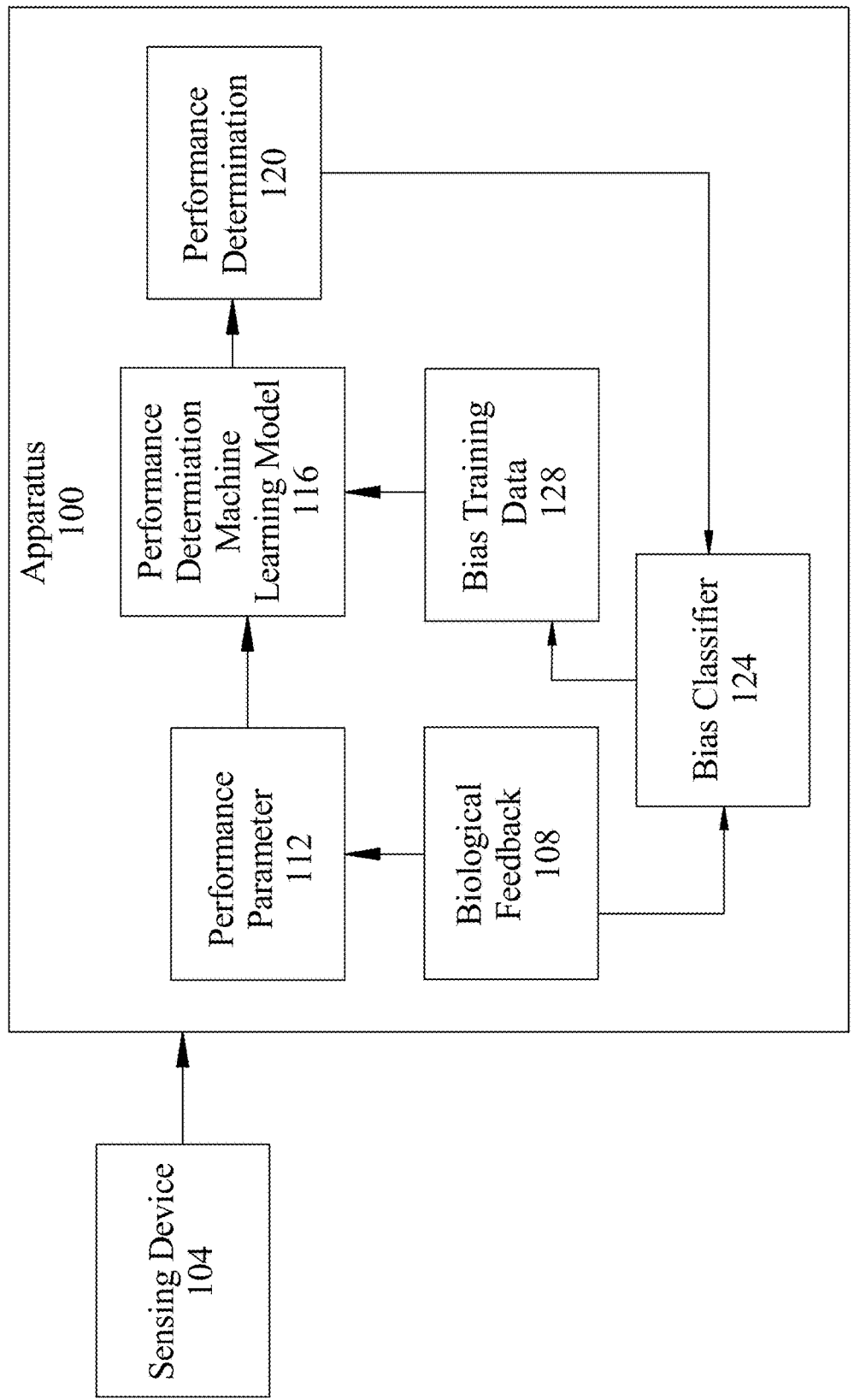
FIG. 1 is an exemplary embodiment of a block diagram of an apparatus for bias eliminated performance determinations.

Referring now to FIG. 1, an exemplary embodiment of apparatus 100 for bias eliminated performance determination is illustrated. In some embodiments, apparatus 100 may include at least a processor and a memory communicatively connected to the at least a processor. A memory may include instructions configuring at least a processor to perform various tasks. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected.

Still referring to FIG. 1, apparatus 100 may include a computing device. Apparatus 100 may include any computing device as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of system 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, in some embodiments, apparatus 100 may be in communication with sensing device 104. A "sensing device" as used in this disclosure is a device capable of detecting elements of the physical world. Elements of the physical world may include, but are not limited to, electromagnetics, vibrations, accelerations, kinetics, biology, and the like. Sensing device 104 may include, but is not limited to, thermometers, cameras, accelerometers, ohmmeters, voltmeters, ammeters, inertial measurement units (IMU), pressure sensors, and the like. Sensing device 104 may include, without limitation, near-infrared (near-IR) spectrometers, exhalation sensors, inhalation sensors, skin temperature and conductance sensors, speech pattern sensors, eye movement sensors, and/or other sensors. In some embodiments, sensing device 104 may include at least a cutaneous sensor that includes a skin galvanic sensor. A "cutaneous sensor" is a device that is configured to detect a cutaneous parameter as a function of a cutaneous phenomenon. A cutaneous sensor may be configured to detect at least a cutaneous parameter as a function of a cutaneous phenomenon. As used in this disclosure, a "cutaneous parameter" is a representation of a cutaneous phenomenon. Exemplary cutaneous parameters include, without limitation, measures skin temperature, galvanic skin response, and the like. As used in this disclosure, a "cutaneous phenomenon" is an occurrence that relates to, or is associated with, the skin. Exemplary cutaneous phenomenon includes, without limitation, skin temperature, electrical conductivity of skin, skin moisture, galvanic skin response and the like. A skin galvanic sensor may be configured to detect a skin galvanic response as a function of a cutaneous electrical characteristic. As used in the current disclosure, "galvanic skin response" (GSR) is a cutaneous phenomenon that causes variation in the electrical characteristics of the skin or the cutaneous phenomenon's representation as a cutaneous parameter. GSR may also refer to a recorded electrical resistance between two electrodes when a very weak current is steadily passed between them. GSR may also be referred to as skin conductance, galvanic skin response (GSR), electrodermal response (EDR), psychogalvanic reflex (PGR), skin conductance response (SCR), sympathetic skin response (SSR), and skin conductance level (SCL). Under GSR, skin resistance may vary with the state of sweat glands in the skin. Sweating may be controlled by the sympathetic nervous system, and skin conductance may be an indication of psychological or physiological arousal. If a sympathetic branch of an autonomic nervous system is highly aroused, then sweat gland activity may increase. This in turn increases skin conductance. In this way, skin conductance may be a measure of emotional and sympathetic responses. GSR may represent a relationship between emotional arousal and sympathetic activity, although electrical change alone may not identify which specific emotion is being elicited. These autonomic sympathetic changes may alter sweat and blood flow, which in turn affects GSR. The number of sweat glands varies across the human body, being highest in hand and foot regions. In some embodiments a cutaneous sensor may account for the number of sweat glands that are present in a given area. The response of the skin and muscle tissue to external and internal stimuli can cause conductance to vary by several microsiemens. Sensing device 104 may detect, transmit, record and/or display these subtle changes. In other embodiments, a galvanic skin sensor may be configured to detect changes between electrodermal resistance and electrodermal potential. A galvanic skin sensor may use a plurality of electrodes; the electrodes may be placed about a distance apart (e.g., an inch apart). In some embodiments, a galvanic skin sensor may measure electrodermal resistance between plurality of electrodes. In some embodiments, a galvanic skin sensor may measure electrodermal potential between plurality of electrodes. In some embodiments, a galvanic skin sensor may measure electrodermal current between plurality of electrodes. In some embodiments, resistance measured by a galvanic skin sensor may vary according to emotional state of user. In other embodiments, a galvanic skin senor may further be configured to detect Galvanic skin potential (GSP). GSP refers to potential (e.g., voltage) measured between two electrodes without any externally applied current. GSP may be measured by connecting electrodes to an amplifier. In some cases, GSP may vary with the emotional state of the subject.

Still referring to FIG. 1, in some embodiments, sensing device 104 may additionally include a physiological sensor in communication with apparatus 100. As used in this disclosure, a "physiological sensor" is a device configured to detect a physiological parameter as a function of a physiological state. A physiological sensor may be configured to detect at least a physiological parameter as a function of a physiological state. In some cases, apparatus 100 may be further configured to determine at least a user performance parameter as a function of physiological parameter. A physiological sensor may include at least a sensor. In an embodiment, sensor may include a baroreceptor, temperature sensor, brain activity sensors, pressure sensors, skin sensors, heart rate sensor, blood pressure sensor, sweat sensor, resistance sensor, voltage sensor, multimeters, and the like. As used in this disclosure, a "sensor" is a device that is configured to detect information as a function of a phenomenon; in some cases, a sensor may also transmit the detected information. For example, in some cases a sensor may transduce a detected phenomenon, such as without limitation, current, speed, direction, force, torque, moisture, temperature, pressure, geographic location, the physical state of the user, and the like, into a sensed signal. Sensor may include one or more sensors which may be the same, similar, or different. Sensor may include one or more sensor suites with sensors in each sensor suite being the same, similar, or different. A physiological sensor may be configured to detect at least a physiological parameter. As used in the current disclosure, a "physiological parameter" includes detection of any datum describing a physiological state of user. As used in the current disclosure, a "physiological state" is a physical condition associated with the user. A physiological state may be associated with a data element describing the users physical or mental health.

Still referring to FIG. 1, at least a physiological parameter may include at least a circulatory parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things.

Still referring to FIG. 1, an exemplary physiological sensor may include a cranial blood oxygen sensor, for example as described in U.S. patent application Ser. No. 16/859,483, entitled "SYSTEMS AND METHODS FOR MEASURING PHYSIOLOGICAL PARAMETERS," filed on Apr. 27, 2020, the entirety of which is incorporated in this disclosure by reference. Another exemplary physiological sensor may include an exhalation sensor, for example as described in U.S. Pat. No. 11,172,845, entitled "COMBINED EXHALED AIR AND ENVIRONMENTAL GAS SENSOR APPARATUS," filed Jul. 20, 2020, the entirety of which is incorporated in this disclosure by reference. Yet another exemplary physiological sensor may include an inhalation sensor, for example as described in U.S. patent application Ser. No. 17/333,169, entitled "INHALATION SENSOR APPARATUS FOR MOBILE RESPIRATION EQUIPMENT," filed on May 28, 2021, the entirety of which is incorporated in this disclosure by reference.

Still referring to FIG. 1, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Still referring to FIG. 1, in some embodiments, a physiological sensor may include a neural activity sensor. A neural activity sensor, as used herein, includes any sensor configured to detect electrical or magnetic phenomena generated by neurons, including cranial neurons such as those located in the brain or brainstem. Neural activity sensor may include an electroencephalographic sensor. Neural activity sensor may include a magnetoencephalographic sensor. In an embodiment, neural activity sensor may be configured to detect neural oscillations. At least a sensor may include an eye-tracking sensor, such as one or more cameras for tracking the eyes of user. Eye-tracking sensor may include, as a non-limiting example, one or more electromyographic (EMG) sensors, which may detect electrical activity of eye muscles; electrical activity may indicate activation of one or more eye muscles to move the eye and used by a circuit such as an alert circuit as described below to determine a movement of user's eyeball, and thus its current location of focus.

Still referring to FIG. 1, in some embodiments, sensing device 104 may be configured to receive biological feedback 108. "Biological feedback" as used in this disclosure is one or more characteristics of an individual's physiology. Biological feedback 108 may include, without limitation, eye movements, speech patterns, heart rates, skin temperatures, skin conductivity values, and the like. Sensing device 104 may include at least an eye sensor. As used in this disclosure, an "eye sensor" is any system or device that is configured or adapted to detect an eye parameter as a function of an eye phenomenon. In some cases, at least an eye sensor may be configured to detect at least an eye parameter as a function of at least an eye phenomenon. As used in this disclosure, an "eye parameter" is an element of information associated with an eye. Exemplary non-limiting eye parameters may include blink rate, eye-tracking parameters, pupil location, gaze directions, pupil dilation, and the like. Exemplary eye parameters are described in greater detail below. In some cases, an eye parameter may be transmitted or represented by an eye signal. An eye signal may include any signal described in this disclosure. As used in this disclosure, an "eye phenomenon" may include any observable phenomenon associated with an eye, including without limitation focusing, blinking, eye-movement, and the like. An eye sensor may include any sensor described in this disclosure. In some embodiments, at least an eye sensor may include an electromyography sensor. An electromyography sensor may be configured to detect at least an eye parameter as a function of at least an eye phenomenon.

Still referring to FIG. 1, in some embodiments, an eye sensor may include an optical eye sensor. An optical eye sensor may be configured to detect at least an eye parameter as a function of at least an eye phenomenon. In some cases, an optical eye sensor may include a camera directed toward one or both of person's eyes. In some cases, optical eye sensor may include a light source, likewise directed to person's eyes. Light source may have a non-visible wavelength, for instance infrared or near-infrared. In some cases, a wavelength may be selected which reflects at an eye's pupil (e.g., infrared). Light that selectively reflects at an eye's pupil may be detected, for instance by camera. Images of eyes may be captured by camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object (e.g., person 108 or person's eyes). In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively where "image" is used as a verb, in this disclosure, it refers to generation and/or formation of an image.

Still referring to FIG. 1, an exemplary camera may include an OpenMV Cam H7 from OpenMV, LLC of Atlanta, Georgia, U.S.A. OpenMV Cam includes a small, low power, microcontroller which allows execution of processes. OpenMV Cam comprises an ARM Cortex M7 processor and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detect motion, for example by way of frame differencing algorithms; detect markers, for example blob detection; detect objects, for example face detection; track eyes; detection persons, for example by way of a trained machine learning model; detect camera motion, for example by way of optical flow detection; detect and decode barcodes; capture images; and record video.

Still referring to FIG. 1, in some cases, a camera may be used to determine eye patterns (e.g., track eye movements). For instance, a camera may capture images and a processor (internal or external) to camera may process images to track eye movements. In some embodiments, a video-based eye tracker may use corneal reflection (e.g., first Purkinje image) and a center of pupil as features to track over time. A more sensitive type of eye-tracker, a dual-Purkinje eye tracker, may use reflections from a front of cornea (i.e., first Purkinje image) and back of lens (i.e., fourth Purkinje image) as features to track. A still more sensitive method of tracking may include use of image features from inside eye, such as retinal blood vessels, and follow these features as the eye rotates. In some cases, optical methods, particularly those based on video recording, may be used for gaze-tracking and may be non-invasive and inexpensive. For instance, in some cases a relative position between camera and person may be known or estimable. Pupil location may be determined through analysis of images (either visible or infrared images). In some cases, camera may focus on one or both eyes and record eye movement as viewer looks. In some cases, eye-tracker may use center of pupil and infrared/near-infrared non-collimated light to create corneal reflections (CR). A vector between pupil center and corneal reflections can be used to compute a point of regard on surface (i.e., a gaze direction). In some cases, a simple calibration procedure with an individual person may be needed before using an optical eye tracker. In some cases, two general types of infrared/near-infrared (also known as active light) eye-tracking techniques can be used: bright-pupil (light reflected by pupil) and dark-pupil (light not reflected by pupil). Difference between bright-pupil and dark pupil images may be based on a location of illumination source with respect to optics. For instance, if illumination is coaxial with optical path, then eye may act as a retroreflector as the light reflects off retina creating a bright pupil effect similar to red eye. If illumination source is offset from optical path, then pupil may appear dark because reflection from retina is directed away from camera. In some cases, bright-pupil tracking creates greater iris/pupil contrast, allowing more robust eye-tracking with all iris pigmentation, and greatly reduces interference caused by eyelashes and other obscuring features. In some cases, bright-pupil tracking may also allow tracking in lighting conditions ranging from total darkness to very bright.

Still referring to FIG. 1, alternatively, in some cases, a passive light optical eye tracking method may be employed. Passive light optical eye tracking may use visible light to illuminate. In some cases, passive light optical tracking yields less contrast of pupil than with active light methods; therefore, in some cases, a center of iris may be used for calculating a gaze vector. In some cases, a center of iris determination requires detection of a boundary of iris and sclera (e.g., limbus tracking). In some case, eyelid obstruction of iris and our sclera may challenge calculations of an iris center. Some optical eye tracking systems may be head-mounted, some may require the head to be stable, and some may function remotely and automatically track the head during motion. Optical eye tracking systems may capture images at frame rate. Exemplary frame rates include 15, 30, 60, 120, 240, 350, 1000, and 1250 Hz.

Still referring to FIG. 1, in some embodiments, biological feedback 108 may include, without limitation, kinetic metrics of an individual. "Kinetic metrics" as used in this discourse are values associated with physical forces. Kinetic metrics may include, without limitation, push forces, pull forces, postures, hand-eye coordination, hand placement, finger movement, shoulder movement, rotational forces, and the like. Kinetic metrics may be measured through physical sensors of sensing device 104 and/or through machine vision estimations. Apparatus 100 may include a machine vision system. A machine vision system may include at least a camera. A machine vision system may use images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

Still referring to FIG. 1, in some embodiments, apparatus 100 may determine one or more kinetic metrics of one or more individuals through a machine vision system. In some embodiments, a machine vision system may be configured to implement a pose estimation technique. A "pose estimation technique" as used in this disclosure is a computer vision process of predicting and tracking a location of an individual or object. A pose estimation technique may include, but is not limited to, bottom-up approaches, top-down approaches, 2D pose estimation, 3D pose estimation, and the like. In some embodiments, a pose estimation technique may include, without limitation, kinematic models, planar models, and/or volumetric models. Apparatus 100 may be configured to utilize a pose estimation machine learning model. A pose estimation machine learning model may be trained with training data correlating optical data to pose estimations. Training data may be received from user input, external computing devices, and/or previous iterations of processing. A pose estimation machine learning model may input image data and output pose estimations. Apparatus 100 may be configured to perform a skeletal analysis of motion of one or more individuals. A skeletal analysis of motion may include generating a skeleton-based model of an individual. A skeleton-based model may include one or more sets of key points of kinematic analysis, such as but not limited to ankles, knees, shoulders, elbows, wrists, and/or limb orientations. Apparatus 100 may be configured to utilize a skeletal analysis machine learning model. A skeletal analysis machine learning model may be trained with training data correlating optical data to skeletal analysis. Training data may be received through user input, external computing devices, and/or previous iterations of processing. A skeletal analysis machine learning model may be configured to input optical data and output skeletal analysis. Apparatus 100 may utilize a skeletal analysis of motion to determine and/or predict performance parameter 112 such as, but not limited to, positioning, dimensions, and the like. For instance and without limitation, procedural performance parameter 112 may include data related to hand positioning of an individual. Hand positioning may include an alignment of hands, fingers, palms, and the like. In some embodiments, hand positioning may include positioning relative to another object or individual. For instance and without limitation, hand positioning may include an alignment of one or more hands on a controlling stick of an airplane.

Still referring to FIG. 1, in some embodiments, apparatus 100 may determine biological feedback 108 from sensing devices 104. Apparatus 100 may receive an audio component from sensing device 104. An "audio component" as used in this disclosure is any input relating to sounds. Audio components may be received through one or more microphones of sensing device 104. As used in this disclosure, a "microphone" is any transducer configured to transduce pressure change phenomenon to a signal, for instance a signal representative of a parameter associated with the phenomenon. A microphone, according to some embodiments, may include a transducer configured to convert sound into electrical signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). A microphone may include any microphone for transducing pressure changes, as described above; therefore, a microphone may include any variety of microphone, including any of: condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone.

Still referring to FIG. 1, an "audio signal," as used in this disclosure, is a representation of sound. In some cases, an audio signal may include an analog electrical signal of time-varying electrical potential. In some embodiments, an audio signal may be communicated (e.g., transmitted and/or received) by way of an electrically transmissive path (e.g., conductive wire), for instance an audio signal path. Alternatively or additionally, audio signal may include a digital signal of time-varying digital numbers. In some cases, a digital audio signal may be communicated (e.g., transmitted and/or received) by way of any of an optical fiber, at least an electrically transmissive path, and the like. In some cases, a line code and/or a communication protocol may be used to aid in communication of a digital audio signal. Exemplary digital audio transports include, without limitation, Alesis Digital Audio Tape (ADAT), Tascam Digital Interface (TDIF), Toshiba Link (TOSLINK), Sony/Philips Digital Interface (S/PDIF), Audio Engineering Society standard 3 (AES3), Multichannel Audio Digital Interface (MADI), Musical Instrument Digital Interface (MIDI), audio over Ethernet, and audio over IP. Audio signals may represent frequencies within an audible range corresponding to ordinary limits of human hearing, for example substantially between about 20 and about 20,000 Hz. According to some embodiments, an audio signal may include one or more parameters, such as without limitation bandwidth, nominal level, power level (e.g., in decibels), and potential level (e.g., in volts). In some cases, relationship between power and potential for an audio signal may be related to an impedance of a signal path of the audio signal. In some cases, a signal path may single-ended or balanced.

With continued reference to FIG. 1, a microphone may be configured to transduce an environmental noise to an environmental noise signal. In some cases, environmental noise may include any of background noise, ambient noise, aural noise, such as noise heard by a user's ear, and the like. Additionally or alternatively, in some embodiments, environmental noise may include any noise present in an environment, such as without limitation an environment surrounding, proximal to, or of interest/disinterest to a user. Environmental noise may, in some cases, include substantially continuous noises, such as a drone of an engine. Alternatively or additionally, in some cases, environmental noise may include substantially non-continuous noises, such as spoken communication or a backfire of an engine. Environmental noise signals may include any type of signal, for instance types of signals described in this disclosure. For instance, an environmental noise signal may include a digital signal or an analog signal.

Still referring to FIG. 1, in some embodiments, audio components received through sensing device 104 may include, but are not limited to, vocalizations of a user, background noises, and the like. Apparatus 100 may be configured to determine speech patterns of an individual through an audio component received from sensing device 104. In some embodiments, automatic speech recognition may require training (i.e., enrollment). In some cases, training an automatic speech recognition model may require an individual speaker to read text or isolated vocabulary. In some cases, a solicitation video may include an audio component having an audible verbal content, the contents of which are known a priori by apparatus 100. Apparatus 100 may then train an automatic speech recognition model according to training data which includes audible verbal content correlated to known content. In this way, apparatus 100 may analyze a person's specific voice and train an automatic speech recognition model to the person's speech, resulting in increased accuracy. Alternatively or additionally, in some cases, apparatus 100 may include an automatic speech recognition model that is speaker-independent. As used in this disclosure, a "speaker independent" automatic speech recognition process does not require training for each individual speaker. Conversely, as used in this disclosure, automatic speech recognition processes that employ individual speaker specific training are "speaker dependent."

Still referring to FIG. 1, in some embodiments, an automatic speech recognition process may perform voice recognition or speaker identification. As used in this disclosure, "voice recognition" refers to identifying a speaker, from audio content, rather than what the speaker is saying. In some cases, apparatus 100 may first recognize a speaker of verbal audio content and then automatically recognize speech of the speaker, for example by way of a speaker dependent automatic speech recognition model or process. In some embodiments, an automatic speech recognition process can be used to authenticate or verify an identity of a speaker. In some cases, a speaker may or may not include subject. For example, subject may speak within solicitation video, but others may speak as well.

Still referring to FIG. 1, in some embodiments, an automatic speech recognition process may include one or all of acoustic modeling, language modeling, and statistically-based speech recognition algorithms. In some cases, an automatic speech recognition process may employ hidden Markov models (HMMs). As discussed in greater detail below, language modeling such as that employed in natural language processing applications like document classification or statistical machine translation, may also be employed by an automatic speech recognition process.

Still referring to FIG. 1, an exemplary algorithm employed in automatic speech recognition may include or even be based upon hidden Markov models. Hidden Markov models (HMMs) may include statistical models that output a sequence of symbols or quantities. HMMs can be used in speech recognition because a speech signal can be viewed as a piecewise stationary signal or a short-time stationary signal. For example, over a short time scale (e.g., 10 milliseconds), speech can be approximated as a stationary process. Speech (i.e., audible verbal content) can be understood as a Markov model for many stochastic purposes.

Still referring to FIG. 1, in some embodiments HMMs can be trained automatically and may be relatively simple and computationally feasible to use. In an exemplary automatic speech recognition process, a hidden Markov model may output a sequence of n-dimensional real-valued vectors (with n being a small integer, such as 10), at a rate of about one vector every 10 milliseconds. Vectors may consist of cepstral coefficients. A cepstral coefficient requires using a spectral domain. Cepstral coefficients may be obtained by taking a Fourier transform of a short time window of speech yielding a spectrum, decorrelating the spectrum using a cosine transform, and taking first (i.e., most significant) coefficients. In some cases, an HMM may have in each state a statistical distribution that is a mixture of diagonal covariance Gaussians, yielding a likelihood for each observed vector. In some cases, each word, or phoneme, may have a different output distribution; an HMM for a sequence of words or phonemes may be made by concatenating an HMMs for separate words and phonemes.

Still referring to FIG. 1, in some embodiments, an automatic speech recognition process may use various combinations of a number of techniques in order to improve results. In some cases, a large-vocabulary automatic speech recognition process may include context dependency for phonemes. For example, in some cases, phonemes with different left and right context may have different realizations as HMM states. In some cases, an automatic speech recognition process may use cepstral normalization to normalize for different speakers and recording conditions. In some cases, an automatic speech recognition process may use vocal tract length normalization (VTLN) for male-female normalization and maximum likelihood linear regression (MLLR) for more general speaker adaptation. In some cases, an automatic speech recognition process may determine so-called delta and delta-delta coefficients to capture speech dynamics and might use heteroscedastic linear discriminant analysis (HLDA). In some cases, an automatic speech recognition process may use splicing and a linear discriminate analysis (LDA)-based projection, which may include heteroscedastic linear discriminant analysis or a global semi-tied covariance transform (also known as maximum likelihood linear transform [MLLT]). In some cases, an automatic speech recognition process may use discriminative training techniques, which may dispense with a purely statistical approach to HMM parameter estimation and instead optimize some classification-related measure of training data; examples may include maximum mutual information (MMI), minimum classification error (MCE), and minimum phone error (MPE).

Still referring to FIG. 1, in some embodiments, an automatic speech recognition process may be said to decode speech (i.e., audible verbal content). Decoding of speech may occur when an automatic speech recognition system is presented with a new utterance and must compute a most likely sentence. In some cases, speech decoding may include a Viterbi algorithm. A Viterbi algorithm may include a dynamic programming algorithm for obtaining a maximum aposteriori probability estimate of a most likely sequence of hidden states (i.e., Viterbi path) that results in a sequence of observed events. Viterbi algorithms may be employed in context of Markov information sources and hidden Markov models. A Viterbi algorithm may be used to find a best path, for example using a dynamically created combination hidden Markov model, having both acoustic and language model information, using a statically created combination hidden Markov model (e.g., finite state transducer [FST] approach).

Still referring to FIG. 1, in some embodiments, speech (i.e., audible verbal content) decoding may include considering a set of good candidates and not only a best candidate, when presented with a new utterance. In some cases, a better scoring function (i.e., re-scoring) may be used to rate each of a set of good candidates, allowing selection of a best candidate according to this refined score. In some cases, a set of candidates can be kept either as a list (i.e., N-best list approach) or as a subset of models (i.e., a lattice). In some cases, re-scoring may be performed by optimizing Bayes risk (or an approximation thereof). In some cases, re-scoring may include optimizing for sentence (including keywords) that minimizes an expectancy of a given loss function with regards to all possible transcriptions. For example, re-scoring may allow selection of a sentence that minimizes an average distance to other possible sentences weighted by their estimated probability. In some cases, an employed loss function may include Levenshtein distance, although different distance calculations may be performed, for instance for specific tasks. In some cases, a set of candidates may be pruned to maintain tractability.

Still referring to FIG. 1, in some embodiments, an automatic speech recognition process may employ dynamic time warping (DTW)-based approaches. Dynamic time warping may include algorithms for measuring similarity between two sequences, which may vary in time or speed. For instance, similarities in walking patterns would be detected, even if in one video the person was walking slowly and if in another he or she were walking more quickly, or even if there were accelerations and deceleration during the course of one observation. DTW has been applied to video, audio, and graphics—indeed, any data that can be turned into a linear representation can be analyzed with DTW. In some cases, DTW may be used by an automatic speech recognition process to cope with different speaking (i.e., audible verbal content) speeds. In some cases, DTW may allow apparatus 100 to find an optimal match between two given sequences (e.g., time series) with certain restrictions. That is, in some cases, sequences can be "warped" non-linearly to match each other. In some cases, a DTW-based sequence alignment method may be used in context of hidden Markov models.

Still referring to FIG. 1, in some embodiments, an automatic speech recognition process may include a neural network. A neural network may include any neural network, for example those disclosed with reference to FIGS. 2-3. In some cases, neural networks may be used for automatic speech recognition, including phoneme classification, phoneme classification through multi-objective evolutionary algorithms, isolated word recognition, audiovisual speech recognition, audiovisual speaker recognition and speaker adaptation. In some cases. neural networks employed in automatic speech recognition may make fewer explicit assumptions about feature statistical properties than HMMs and therefore may have several qualities making them attractive recognition models for speech recognition. When used to estimate the probabilities of a speech feature segment, neural networks may allow discriminative training in a natural and efficient manner. In some cases, neural networks may be used to effectively classify audible verbal content over short-time interval, for instance such as individual phonemes and isolated words. In some embodiments, a neural network may be employed by automatic speech recognition processes for pre-processing, feature transformation and/or dimensionality reduction, for example prior to HMM-based recognition. In some embodiments, long short-term memory (LSTM) and related recurrent neural networks (RNNs) and Time Delay Neural Networks (TDNN's) may be used for automatic speech recognition, for example over longer time intervals for continuous speech recognition.

Still referring to FIG. 1, in some embodiments, apparatus 100 may determine at least a speech pattern as a function of at least a speech parameter. As used in this disclosure, a "speech pattern" is a representation of a speech-related behavioral phenomenon. In some cases, a speech pattern may be derived or otherwise determined from a speech parameter. Exemplary speech patterns include timber, pitch, and cadence of speech. In some cases, speech pattern may be unrelated to content of an individual's speech. Instead, in some cases, a speech pattern may be related to changes audible characteristics of an individual's speech. In some cases, a speech pattern may be derived through analysis of speech parameters, for instance audio analysis described above. Speech patterns may include one or more prosodic variables. As used in this disclosure, "prosodic variables" are variables that relate to spoken syllables or larger speech units. In some cases, a speech pattern may include audible variables, for instance pitch, change in pitch, length of units of speech (e.g., syllables), volume, loudness, prominence (i.e., relative volume of a unit speech, timbre, quality of sound, and the like. In some cases, a speech pattern may include acoustic terms. Acoustic terms may include without limitation fundamental frequency, duration, intensity, sound pressure, spectral characteristics, and the like. A speech pattern may include speech tempo. As used in this disclosure, "speech tempo" is a measure of a number of speech units within a certain amount of time. Speech tempo may vary within speech of one person, for instance according to context and emotional factors. Speech tempo may have units of syllables per second.

Still referring to FIG. 1, in some embodiments, apparatus 100 may be configured to categorize biological feedback 108 to one or more biologically derived categories. A "biologically derived category" as used in this disclosure is a group of data relating to a physiological element. Apparatus 100 may utilize a classifier and/or other machine learning process, without limitation, to classify biological feedback 108 to biologically derived categories, such as, but not limited to, heart parameters, breathing parameters, mental state parameters, and the like. Apparatus 100 may correlate and/or classify biological feedback 108 to one or more performance parameters 112. Apparatus 100 may determine, as a non-limiting example, that a heart rate of biological feedback 108 belongs to a heart parameters category of a performance parameter. Apparatus 100 may train a classifier with training data correlating biological feedback to biologically derived categories. Training data may be received through user input, external computing devices, and/or previous iterations of processing.

Still referring to FIG. 1, in some embodiments, apparatus 100 may determine performance parameter 112. A "performance parameter" as used in this disclosure is a metric pertaining to a task. A "task" as used in this disclosure is an objective. Tasks may include, but are not limited to, operating cars, planes, boats, motorcycles, and the like. In some embodiments, a task may include operating a fighter pilot jet. A task may include fighter pilot training. "Fighter pilot training" as used in this discourse is a process of improving skill in the field of combat jets. Fighter pilot training may include, but is not limited to, maneuvering a fighter jet, performing evasive maneuvers, training to withstand G forces, and the like. Tasks may include one or more subtasks. A "subtask" as used in this disclosure is a portion of an objective. Subtasks may include, but are not limited to, pre-flight checks, starting engines, engaging safety equipment, performing a turn of a vehicle, halting a motion of a vehicle, and the like. Apparatus 100 and/or performance determination machine learning model 116 may classify and/or categorize tasks and/or subtasks to one or more task categories. A "task category" as used in this disclosure is a classification of a task to a group. Task categories may include, but are not limited to, operations of one or more vehicles, such as turning, braking, accelerating, pivoting, diving, climbing, reversing, and the like. Apparatus 100 may classify subtasks to one or more subtask groupings. Subtask groupings may include, but are not limited to, pre-flight checks, engaging safety equipment, and the like.

Still referring to FIG. 1, performance parameter 112 may include, without limitation, interaction with one or more pilot controls of a plane. Interaction with one or more pilot controls of a plane may include, without limitation, turning, braking, liftoff, landing, climbing, cruising, and the like. In some embodiments, performance parameter 112 may include an operating posture of an individual. An operating posture of an individual may include, without limitation, a spine alignment, head tilt, arm and/or shoulder placement, and the like. In some embodiments, performance parameter 112 may include one or more biological performances of an individual. A "biological performance" as used in this disclosure is a score of a vital sign corresponding to a task. Biological performances may include, without limitation, eye movements of an individual, heart rates, heart rhythms, breathing rates, skin temperatures, skin conductivities, and the like. For instance, and without limitation, a biological performance may include an oxygenation of an individual's blood while experiencing intense gravitational forces (G forces), such as 8 G's.

Still referring to FIG. 1, in some embodiments, apparatus 100 may compare biological feedback 108 to performance parameter 112. Performance parameter 112 may be determined through user input and/or one or more external computing devices, without limitation. In some embodiments, performance parameter 112 may be determined through a machine learning model, such as any machine learning model as described throughout this disclosure, without limitation. In some embodiments, apparatus 100 may categorize biological feedback 108 to one or more performance parameters 112. Apparatus 100 may utilize a performance parameter classifier. A performance parameter classifier may be trained with training data categorizing biological feedback to performance parameters such as, but not limited to, eye movements, postures, hand placements, breathing rates, and the like. Training data may be received through user input, external computing devices, and/or previous iterations of processing. In some embodiments, a performance parameter classifier may be configured to input biological feedback 108 and output one or more classifications of biological feedback 108 to one or more performance parameters 112. As a non-limiting example, sensing device 104 may include a camera and biological feedback 108 may include eye movements of an individual. A performance parameter classifier may classify the eye movements to category of task focusing. A performance parameter classifier may be used by apparatus 100 to parse biological feedback 108 into performance parameter categories, which may allow faster and/or more accurate generation of performance determination 120. A "performance determination" as used in this disclosure is a score of a completion of a task.

Still referring to FIG. 1, in some embodiments, apparatus 100 may generate performance determination machine learning model 116. A "performance determination machine learning model" as used in this disclosure is a machine learning process that outputs performance determinations. Performance determination machine learning model 116 may be trained with training data correlating performance parameters 112 and/or biological feedback 108 to performance determinations 120. Training data may be received from user input, external computing devices, and/or previous iterations of processing. In some embodiments, performance determination machine learning model 116 may be configured input performance parameter 112 and output performance determinations 120. Performance determinations 120 may include one or more values associated with one or more parts of a task. In some embodiments, performance determinations 120 may include scores out of 10, percentages out of 100, words and/or phrases, and the like, without limitation. For instance and without limitation, performance determination 120 may include a score of "adequate" of a task of operating an airplane in cruise mode. In some embodiments, performance determination machine learning model 116 may generate performance determination 120 with a temporal element. A "temporal element" as used in this disclosure is any metric associated with time. A temporal element may include, but is not limited to, microseconds, seconds, minutes, hours, days, and the like. Performance determination machine learning model 116 may provide performance determinations 120 corresponding to temporal elements of a task. For instance, and without limitation, performance determination machine learning model 116 may provide performance determination 120 of 70% at Sep. 12, 2022, 12:26:54 PM of an individual performing a pre-flight check of an aircraft. Performance determination machine learning model 116 may update performance determinations 120 in real time. "Real time" as used in this disclosure is the actual time during which a process or event occurs. Continuing the above example, performance determination machine learning model 116 may update performance determination 120 from 70% to 77% at Sep. 12, 2022, 12:27:04 PM of an individual performing a pre-flight check of an aircraft. Performance determination machine learning model 116 may provide one or more timestamps with one or more performance determinations 120. A "time stamp" as used in this disclosure is a flagged temporal element. A time stamp may include a precise time, range of times, and the like. For instance and without limitation, performance determination machine learning model 116 may output a first performance determination 120 of 8 out of 10 at a first given time and a second performance determination 120 of 9 out of 10 at a second given time. Apparatus 100 and/or performance determination machine learning model 116 may generate a performance timeline. A "performance timeline" as used in this disclosure is a set of one or more points in time associated with a performance of a task. A performance timeline may include, but is not limited to, a single task, a plurality of tasks, a combination of tasks through a day, a combination of tasks throughout a week, and the like.

Still referring to FIG. 1, in some embodiments, apparatus 100 and/or performance determination machine learning model 116 may be additionally configured to determine a confidence metric associated with correlation and/or determination of a cognitive status. As used in this disclosure, a "confidence metric" is a quantified expression of confidence associated with a function, such as a likelihood or probability that an output of a function is accurate or correct. Determination of a confidence metric may include any appropriate process described in this disclosure. A confidence metric may be determined by, without limitation, comparing one or more historical trends, receiving confidence scores through user input, comparing statistical averages, and the like. In some cases, a confidence metric may be a proportional or unitless figure, for example expressed in terms of a proportion or percentage. Alternatively of additionally, a confidence metric may be represented using relative or absolute units. In some cases, a confidence metric may be compared to a threshold confidence metric in order to determine suitability of an associated correlation and/or determination, for example of a cognitive status. For instance, in some cases a confidence metric no less than a threshold confidence metric of 95%, 90%, 85%, 75%, or 50% is required in order to assure an underlying correlation and/or determination of cognitive status is "correct."

Still referring to FIG. 1, in some embodiments, apparatus 100 may generate bias classifier 124. A "bias classifier" as used in this disclosure is a machine learning process that categorizes input data to bias categories. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Apparatus 100 and/or another device may generate a classifier using a classification algorithm, defined as a processes whereby apparatus 100 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, apparatus 100 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) \ P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and P(B) is the probability of the data regardless of the hypothesis. A naïve Bayes algorithm may be generated by first transforming training data into a frequency table. Apparatus 100 may then calculate a likelihood table by calculating probabilities of different data entries and classification labels. Apparatus 100 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, apparatus 100 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, a "bias category" as used in this disclosure is a classification of data for a category or type of bias. Bias classifier 124 may be trained with training data correlating biological feedback and/or performance determinations to categories of bias. Training data may be received through user input, external computing devices, and/or previous iterations of processing. In some embodiments, bias classifier 124 may be configured to input performance determination 120 and/or biological feedback 108 and categorize performance determination 120 and/or biological feedback 108 to one or more bias categories, such as, but not limited to, gender bias, racial bias, and/or other forms of human bias. "Gender bias" as used in this disclosure is a skewing of data attributed by human gender. Gender bias may include, but is not limited to, biases towards, women, men, and the like. For instance and without limitation, a woman may have a cooler skin temperature than a man, which may be misinterpreted as an error in performance determination 120. "Racial bias" as used in this disclosure is a skewing of data interpretation attribute by racial differences of an individual. Racial bias may include, but are not limited to, African Americans, Asian-Americans, Hispanics, Pacific Islanders, Caucasians, and the like. For instance and without limitation, performance determination 120 may flag a pupil dilation incorrectly of an African individual having darker irises than a Caucasian individual having lighter irises.

Still referring to FIG. 1, in some embodiments, bias classifier 124 may generate bias training data 128. "Bias training data" as used in this disclosure is a set of data correlating performance determinations to bias categories. Bias training data 128 may include, without limitation, datasets correlating biological feedback to performance determinations. Bias training data 128 may include modified performance determinations 120 based on biological feedback 108, which may eliminate bias in performance determination machine learning model 116. In some embodiments, performance determination machine learning model 116 may be configured to utilize bias training data 128 to reduce biases in performance determinations 120, such as gender bias, racial bias, and the like.

Figure 2:
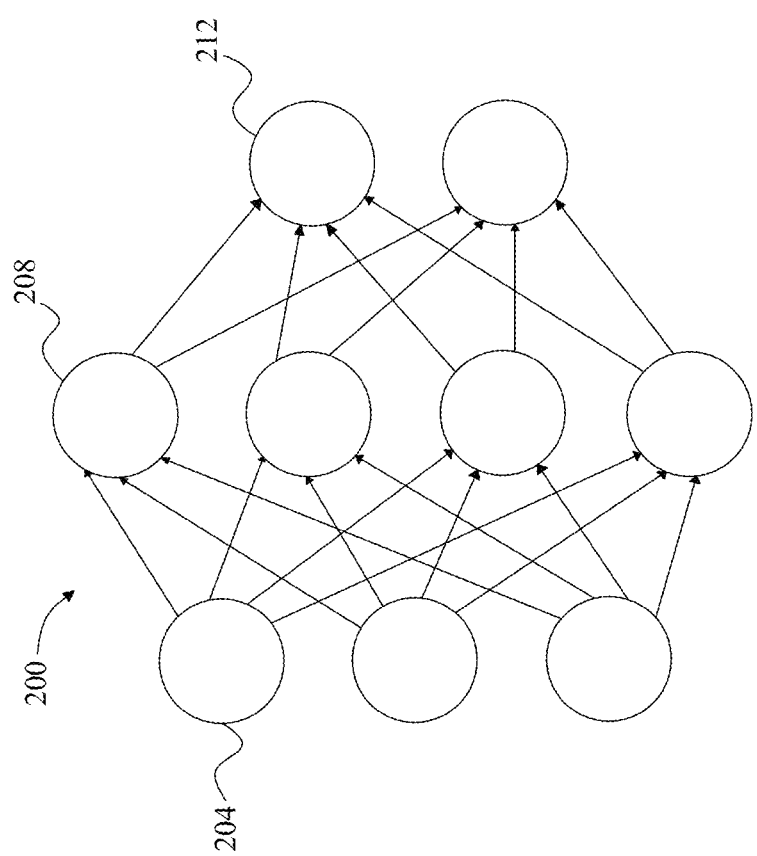
FIG. 2 is an exemplary embodiment of a neural network.

Referring now to FIG. 2, an exemplary embodiment of neural network 200 is illustrated. A neural network 200 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 204, one or more intermediate layers 208, and an output layer of nodes 212. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 3:
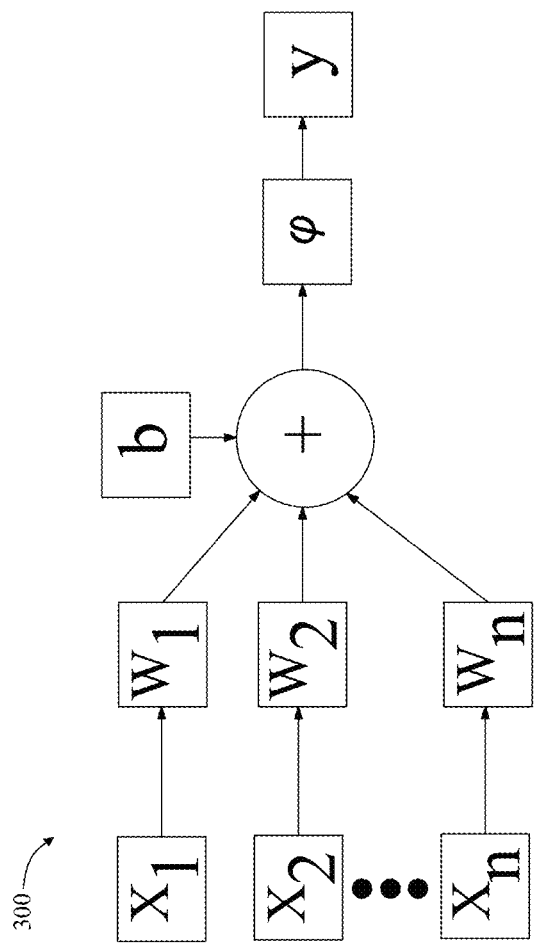
FIG. 3 is an exemplary embodiment of a node of a neural network.

Referring now to FIG. 3, an exemplary embodiment of a node of a neural network is illustrated. A node may include, without limitation a plurality of inputs x; that may receive numerical values from inputs to a neural network containing the node and/or from other nodes. Node may perform a weighted sum of inputs using weights w, that are multiplied by respective inputs xi. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight w, applied to an input x; may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights w, may be determined by training a neural network using training data, which may be performed using any suitable process as described above.

Figure 4:
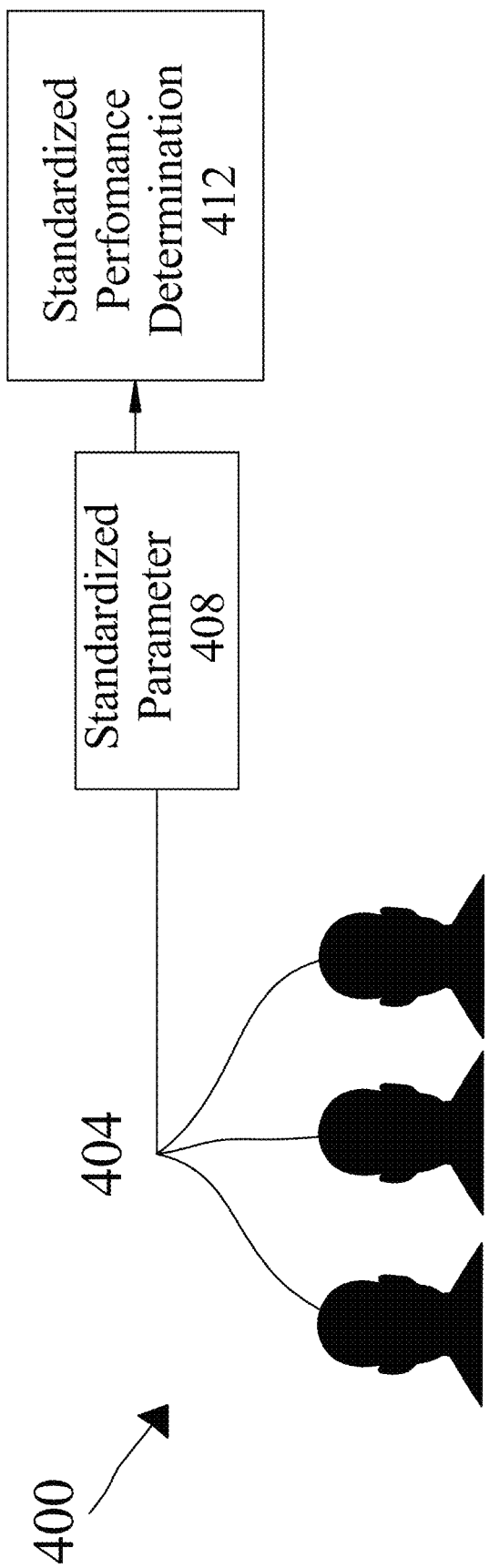
FIG. 4 is an exemplary embodiment of a system for providing a standardized performance determination.

Referring now to FIG. 4, an exemplary embodiment of a system 400 for standardized performance determination is presented. System 400 may include any computing device, machine learning process, classifier, and/or sensing device, as described throughout this disclosure, without limitation. System 400 may include a plurality of individuals 404. Plurality of individuals 404 may include a biologically diverse group of individuals, such as, without limitation, varying ages, genders, races, and the like. For instance, and without limitation, plurality of individuals 404 may include a 34 year old Chinese woman, a 44 year old African American man, and a 22 year old Arabic woman. Apparatus 100 and/or performance determination machine learning model 116, as described above in FIG. 1, may generate standardized parameter 408. A "standardized parameter" as used in this disclosure is a normalized metric. Standardized parameter 408 may include one or more values, sets of values, ranges of values, and the like, without limitation. Apparatus 100 may calculate standardized parameter 408 based on biological feedback, bias classifications, and the like. In some embodiments, standardized parameter 408 may include one or more weighted parameters. A "weighted parameter" as used in this disclosure is a variable having an influence of a total value. Weighted parameters may include, but are not limited to, body temperatures, blood oxygenations, heart rates, eye movements, and the like. For instance and without limitation, a weighted parameter may boost a performance determination of a skin temperature of a petite woman, who may have a lower skin temperature than a large male. Weighted parameters may include, without limitation, values out of 1, values out of 10, values out of 100, and the like. As a non-limiting example, a weighted parameter may include 0.4 for heart rate, 0.2 for skin temperature, and 0.4 for blood pressure, totaling 1. Continuing this example, a change in heart rate may affect a total performance score of an individual more than a change in skin temperature might. Weighted parameters may be calculated using any computing device and/or machine learning model as described throughout this disclosure, without limitation.

Still referring to FIG. 4, in some embodiments, apparatus 100 may calculate standardized performance determination 412 from standardized parameter 408 and/or one or more biological feedback inputs. A "standardized performance determination" as used in this disclosure is a normalized objective completion score. Standardized performance determination 412 may include, without limitation, values out of 1, 5, 10, 100, and the like. In some embodiments, standardized performance determination 412 may include one or more percentages and/or other numeric forms. Apparatus 100 may calculate standardized performance determination 412 to eliminate any racial, gender, and/or other biases. Apparatus 100 may adjust a performance metric of each biologically derived bias associated with plurality of individuals 404 to create standardized performance determination 412. For instance, and without limitation, a woman pilot and a male pilot may perform a task of barrel rolling a fighter jet equally. However, due to biological differences between male and female physiology, a machine learning model may identify a male pilot as performing better than the female pilot, or vice versa. Standardized performance determination 412 may eliminate changes in physiology due to races, genders, and the like, which may allow a more accurate scoring of a task of plurality of individuals 404.

Figure 5:
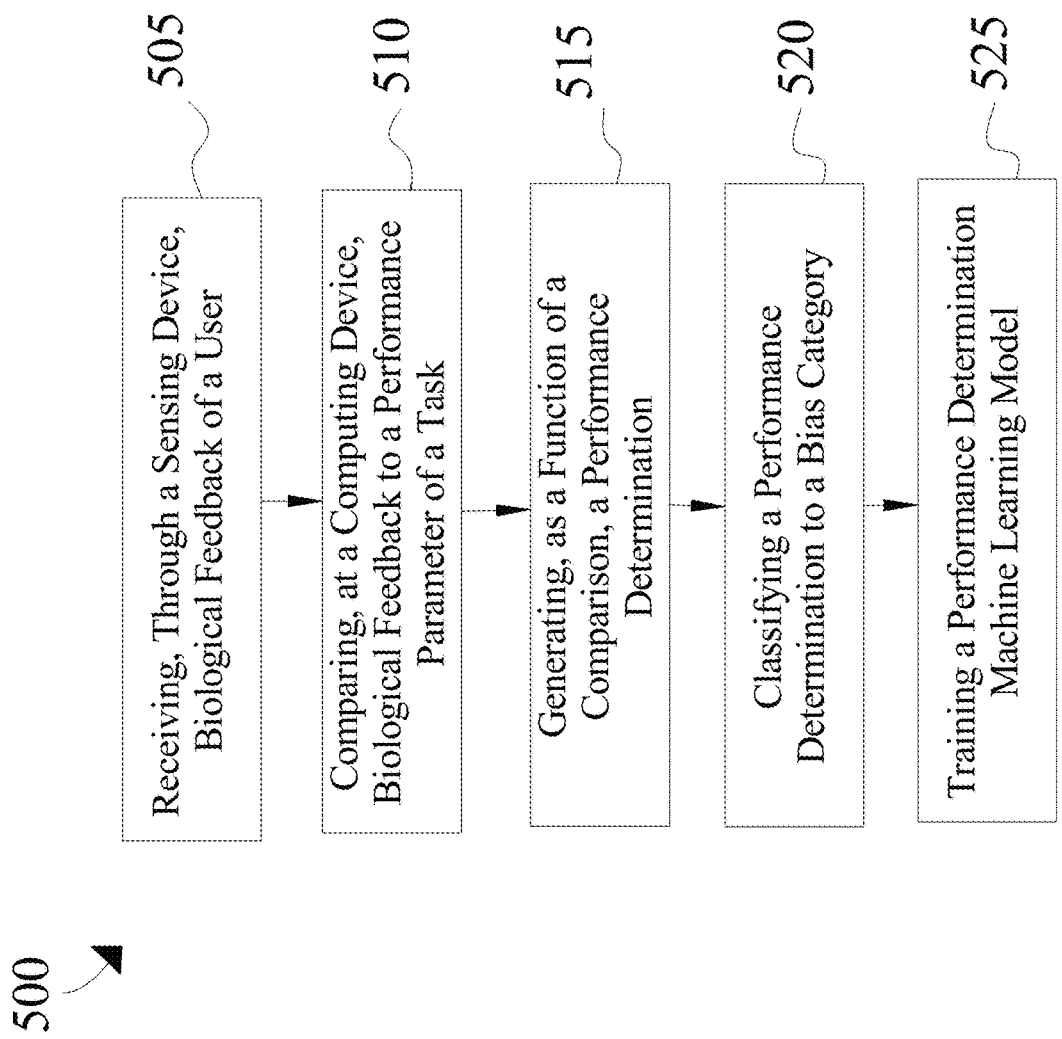
FIG. 5 is an exemplary embodiment of a flowchart of a method of bias eliminated performance determination using a computing device.

Referring now to FIG. 5, a method 500 of bias eliminated performance determination is presented. At step 505, method 500 includes receiving, through a sensing device, biological feedback of a user. A sensing device may include, without limitation, heart rate monitors, thermometers, microphones, and the like. Biological feedback may include, without limitation, vocalizations, heart rates, blood pressures, skin temperatures, and the like. This step may be implemented, without limitation, as described above in FIGS. 1-4.

Still referring to FIG. 5, at step 510, method 500 includes comparing, at a computing device, biological feedback to a performance parameter of task. A performance parameter may include one or more metrics of adequacy, without limitation. A task may include, without limitation, operating a vehicle. This step may be implemented, without limitation, as described above in FIGS. 1-4.

Still referring to FIG. 5, at step 515, method 500 includes generating, as a function of a comparison, a performance determination. A performance determination may include, without limitation, a score of an individual's ability to perform a task. This step may be implemented, without limitation, as described above in FIGS. 1-4.

Still referring to FIG. 5, at step 520, method 500 includes classifying a performance determination to a bias category.

A performance determination may be classified to a bias category using a bias classifier. Bias categories may include, without limitation, racial bias, gender bias, and the like. This step may be implemented, without limitation, as described above in FIGS. 1-4.

Still referring to FIG. 5, at step 525, method 500 includes training a performance determination machine learning model. A performance determination machine learning model may be trained with bias training data. Bias training data may include data correlating This step may be implemented, without limitation, as described above in FIGS. 1-4.

Figure 6:
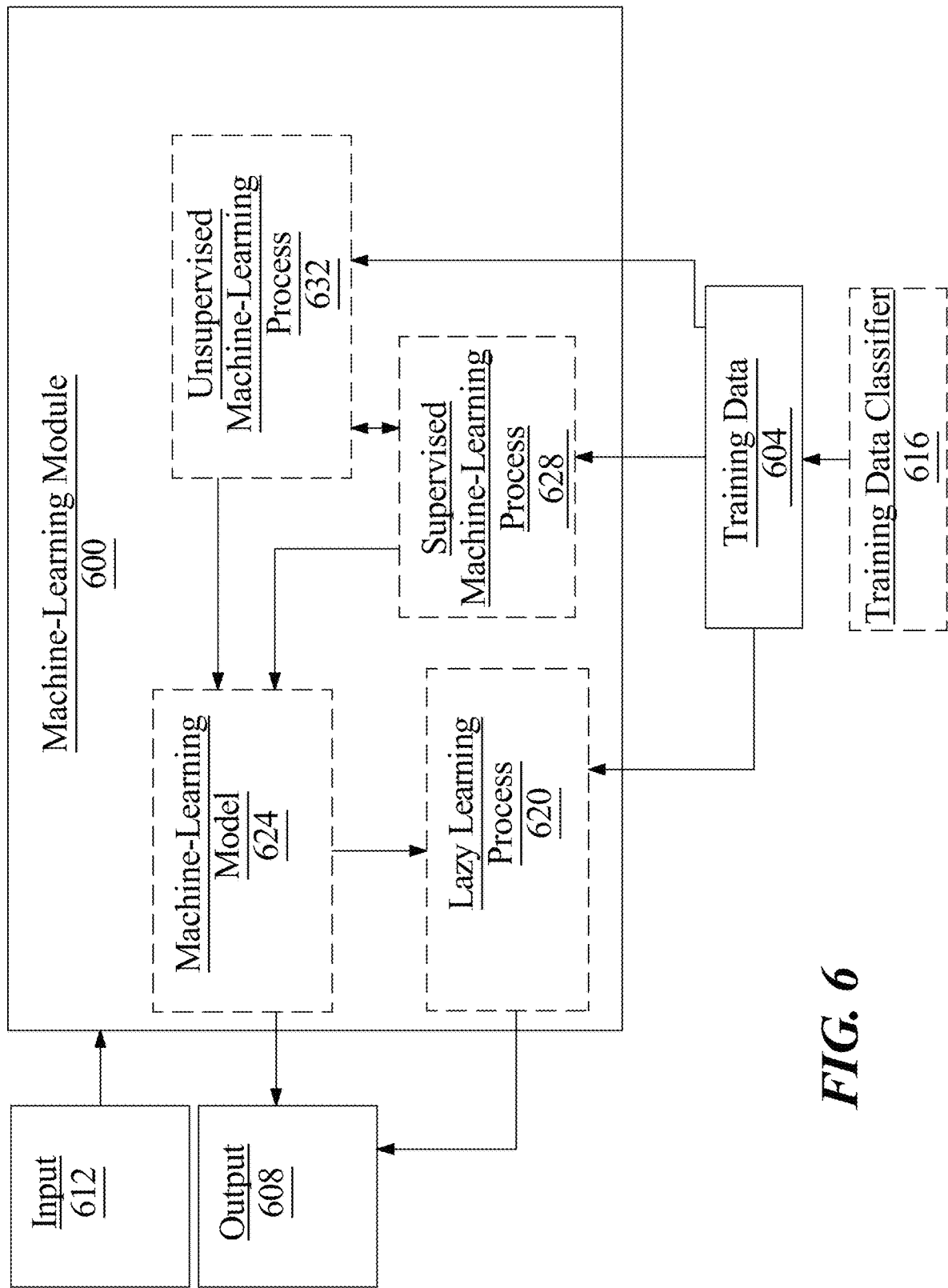
FIG. 6 is a block diagram of a machine-learning module in accordance with one or more embodiments of the present disclosure.

Referring now to FIG. 6, an exemplary embodiment of a machine-learning module 600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 604 to generate an algorithm that will be performed by a computing device/module to produce outputs 608 given data provided as inputs 612; this is in contrast to a non-machine learning software program where the commands to be executed are determined in advance by a user and written in a programming language.

Still referring to FIG. 6, "training data," as used herein, is data containing correlations that a machine-learning process may use to model relationships between two or more categories of data elements. For instance, and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure. As a non-limiting illustrative example inputs may include biological feedback and outputs may include one or more performance determinations.

Further referring to FIG. 6, training data may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 600 may generate a classifier using a classification algorithm, defined as a processes whereby a computing device and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to performance parameters, tasks, subtasks, biases, and the like.

Still referring to FIG. 6, machine-learning module 600 may be configured to perform a lazy-learning process 620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include biological feedback as described above as inputs, performance determinations as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above.

Further referring to FIG. 6, machine learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
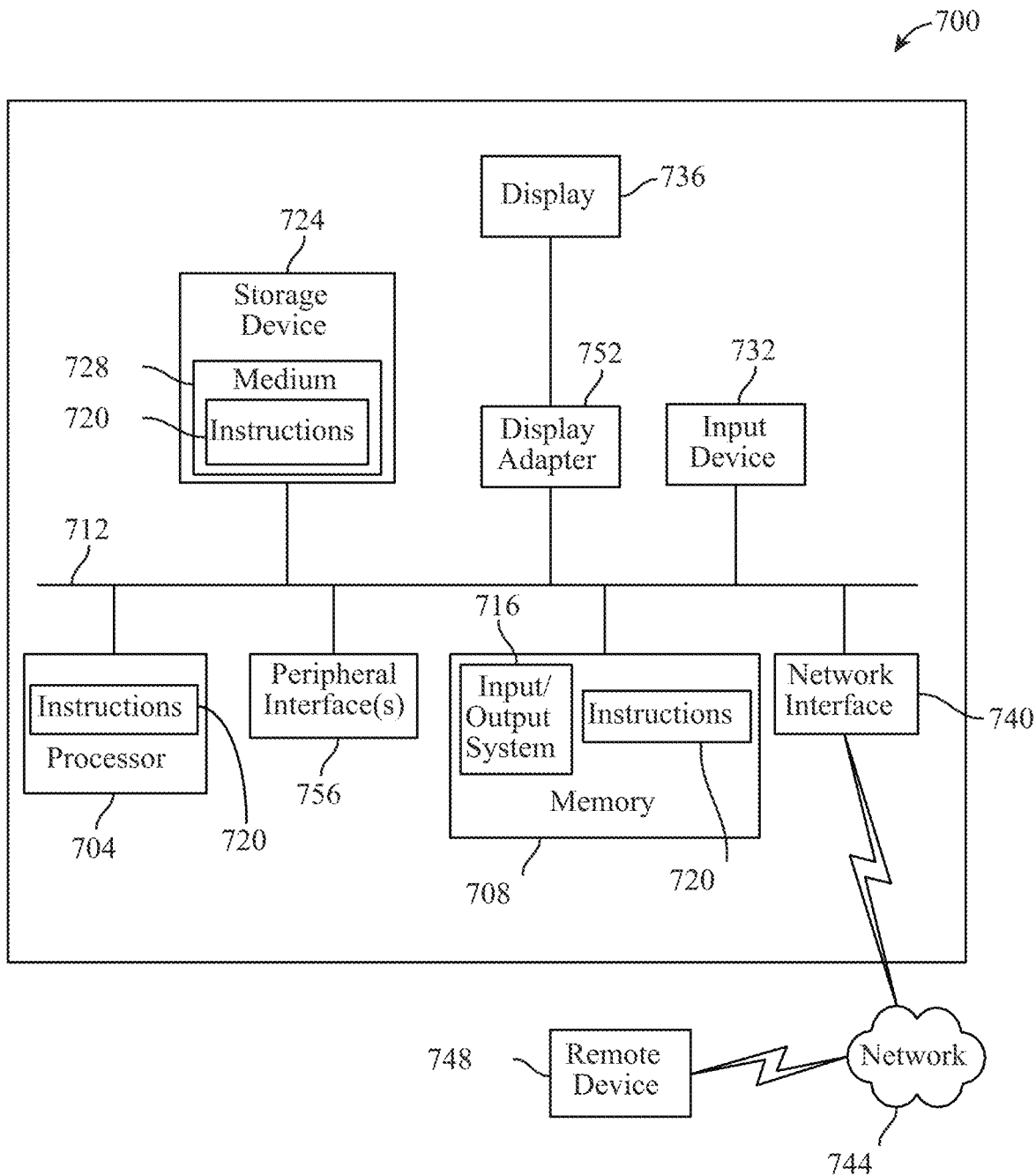
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for bias eliminated performance determination, the apparatus comprising:
   at least a processor; and
   a memory communicatively connected to the at least a processor, the memory containing instructions configuring the at least a processor to:
   receive, using a sensing device comprising a physiological sensor, biological feedback of a user, the biological feedback comprising at least one kinetic metric;
   determine a performance parameter for a task as a function of a skeletal analysis, wherein determining the performance parameter comprises:
   receiving first training data correlating optical data to skeletal analysis data;
   training a skeletal analysis machine learning model as a function of the first training data; and
   outputting the skeletal analysis as a function of the trained skeletal analysis machine learning model;
   compare the biological feedback to the performance parameter for the task;
   generate, as a function of the comparison, a performance determination and a performance timeline for the user using a performance determination machine learning model trained with second training data correlating biological feedbacks to performance determinations;
   classify the performance determination to a bias category as a function of a bias classifier, wherein classifying the performance determination comprises:
   receiving bias training group data, wherein the bias training group data comprises modified performance determinations based on the biological feedback and correlates a plurality of biological feedback data and/or a plurality of performance determination data to categories of bias:
   training, iteratively, the bias classifier using the bias training group data, wherein training the bias classifier includes retraining the bias classifier with feedback from previous iterations of the bias classifier; and classifying the performance determination to the bias category using the trained bias classifier;

eliminate one or more biologically derived biases from the performance determination in response to the classification of the performance determination to the bias category; and display the bias eliminated performance determination to the user.

2. The apparatus of claim 1, wherein the bias classifier is configured to classify the performance determination to a biologically derived category as a function of the biological feedback.

3. The apparatus of claim 1, wherein the performance determination machine learning model is configured to correlate performance determinations with temporal elements of the task.

4. The apparatus of claim 3, wherein the performance determination machine learning model is further configured to flag the performance determinations with the temporal elements of the task across the performance timeline.

5. The apparatus of claim 1, wherein the performance determination machine learning model is configured to determine performance determinations of subtasks of the task.

6. The apparatus of claim 1, wherein the performance determination machine learning model is configured to adjust a performance metric for each biologically derived bias to create a standardized performance metric.

7. The apparatus of claim 1, wherein the sensing device comprises a near-infrared spectrometer.

8. The apparatus of claim 1, wherein the task includes fighter pilot training.

9. A method of bias eliminated performance determination using a computing device, comprising:

receiving, by at least a processor, through a sensing device, biological feedback of a user, the biological feedback comprising at least one kinetic metric;

determining, by the at least a processor a performance parameter for a task as a function of a skeletal analysis, wherein determining the performance parameter comprises:

receiving first training data correlating optical data to skeletal analysis;

training a skeletal analysis machine learning model as a function of the first training data; and outputting the skeletal analysis as a function of the trained skeletal analysis machine learning model;

comparing, at the at least a processor, the biological feedback to a performance parameter for a task;

generate, by the at least a processor, as a function of the comparison, a performance determination and a performance timeline for the user using a performance determination machine learning model trained with training data correlating biological feedback to performance determinations, wherein generating the performance determination and the performance timeline for the user comprises updating the performance determination and generating the performance determination and an updated performance determination;

classify, by the at least a processor, the performance determination to a bias category as a function of a bias classifier, wherein the performance determination comprises:

receiving bias training group data, wherein the bias training group data comprises modified performance determinations based on the biological feedback and correlates a plurality of biological feedback data and/or a plurality of performance determination data to categories of bias;

training, iteratively, the bias classifier using the bias training group data, wherein training the bias classifier includes retraining the bias classifier with feedback from previous iterations of the bias classifier; and classifying the performance determination to the bias category using the trained bias classifier;

eliminating, by the at least a processor, one or more biologically derived biases from the performance determination in response to the classification of the performance determination to the bias category; and displaying, by the at least a processor, the bias eliminated performance determination to the user.

10. The method of claim 9, wherein classifying further comprises classifying the performance determination to a biologically derived category as a function of the biological feedback.

11. The method of claim 9, further comprising correlating, using the performance determination machine learning model, performance determinations with temporal elements of the task.

12. The method of claim 11, further comprising flagging, by the performance determination machine learning model, the performance determinations with the temporal elements of the task across the performance timeline.

13. The method of claim 9, further comprising determining, using the performance determination machine learning model, performance determinations of subtasks of the task.

14. The method of claim 9, wherein the performance determination machine learning model is configured to adjust a performance metric for each biologically derived bias to create a standardized performance metric.

15. The method of claim 9, wherein the sensing device comprises a near-infrared spectrometer.

16. The method of claim 9, wherein the task includes fighter pilot training.

\* \* \* \* \*